United States Patent
Grob et al.

(12) 
(10) Patent No.: US 6,389,879 B1
(45) Date of Patent: May 21, 2002

(54) METHOD, DEVICE AND APPARATUS TO DETECT CHANGES OF STATE IN A CAPILLARY AND TO OPTIMIZE INJECTION CONDITIONS OF A SAMPLE INTO GAS-CHROMATOGRAPHY APPARATUSES

(75) Inventors: Konrad Grob, Fehraltorf (CH); Fausto Munari, Milan; Pier Albino Colombo, Treviglio, both of (IT)

(73) Assignee: Thermoquest Italia, S.p.A., Rodano (IT)

( * ) Notice: Subject to any disclaimer, the term of this patent is extended or adjusted under 35 U.S.C. 154(b) by 0 days.

(21) Appl. No.: 09/260,226

(22) Filed: Mar. 1, 1999

Related U.S. Application Data

(63) Continuation of application No. PCT/EP98/03977, filed on Jun. 30, 1998.

(30) Foreign Application Priority Data

Jul. 2, 1997 (IT) .......................................... MI97A1563

(51) Int. Cl.[7] ......................... G01N 30/18; G01N 30/00
(52) U.S. Cl. .................................... 73/23.42; 073/23.35
(58) Field of Search .............................. 73/23.35, 23.42

(56) References Cited

U.S. PATENT DOCUMENTS

| | | |
|---|---|---|
| 4,422,860 A | 12/1983 | Feinstein |
| 4,702,115 A | 10/1987 | Brabandt et al. ........ 73/864.85 |
| 5,672,810 A | 9/1997 | Shibamoto |

FOREIGN PATENT DOCUMENTS

| | | | |
|---|---|---|---|
| EP | 0355546 | 2/1990 | ................ 73/23.42 |
| EP | 0572968 | 12/1993 | |
| EP | 0783103 | 12/1996 | |
| EP | 0753739 | 1/1997 | |
| EP | 806661 | * 11/1997 | ................ 73/23.42 |
| WO | 9901759 | 1/1999 | ................ 73/23.42 |

OTHER PUBLICATIONS

Grob, et al., "Vaporising Systems For Large Volume Injection Or On–line Transfer Into Gas Chromatography: Classification, Critical Remarks And Suggestions", *Journal of Chromatography*, A 750 (1996) pp. 11–23.

Grob, et al. "Spitless Injection of Large Volumes of Aqueous Samples: Further Experience, Experiments on Analyzing Triazines by Direct Injection of Drinking Water", *2439 HRC Journal of High Resolution Chromatograph 17 (1994)*, Nov., No. 11, vol. 17, Heidelberg, DE, pp. 792–794.

* cited by examiner

*Primary Examiner*—Daniel S. Larkin
(74) *Attorney, Agent, or Firm*—Cobrin & Gittes

(57) ABSTRACT

This invention concerns a method, a device, and an apparatus to detect changes of state in a capillary tube, in particular a gas-chromatographic column or pre-column and to consequently control the conditions under which samples are injected or introduced. The detection is carried out through changes in the temperature of the capillary tube, and/or changes in pressure, or flow rate of the carrier gas.

The invention further concerns a method to control gas-chromatography functions by means of a specially designed software, based on the above-mentioned detections on a sample apparatus.

21 Claims, 6 Drawing Sheets

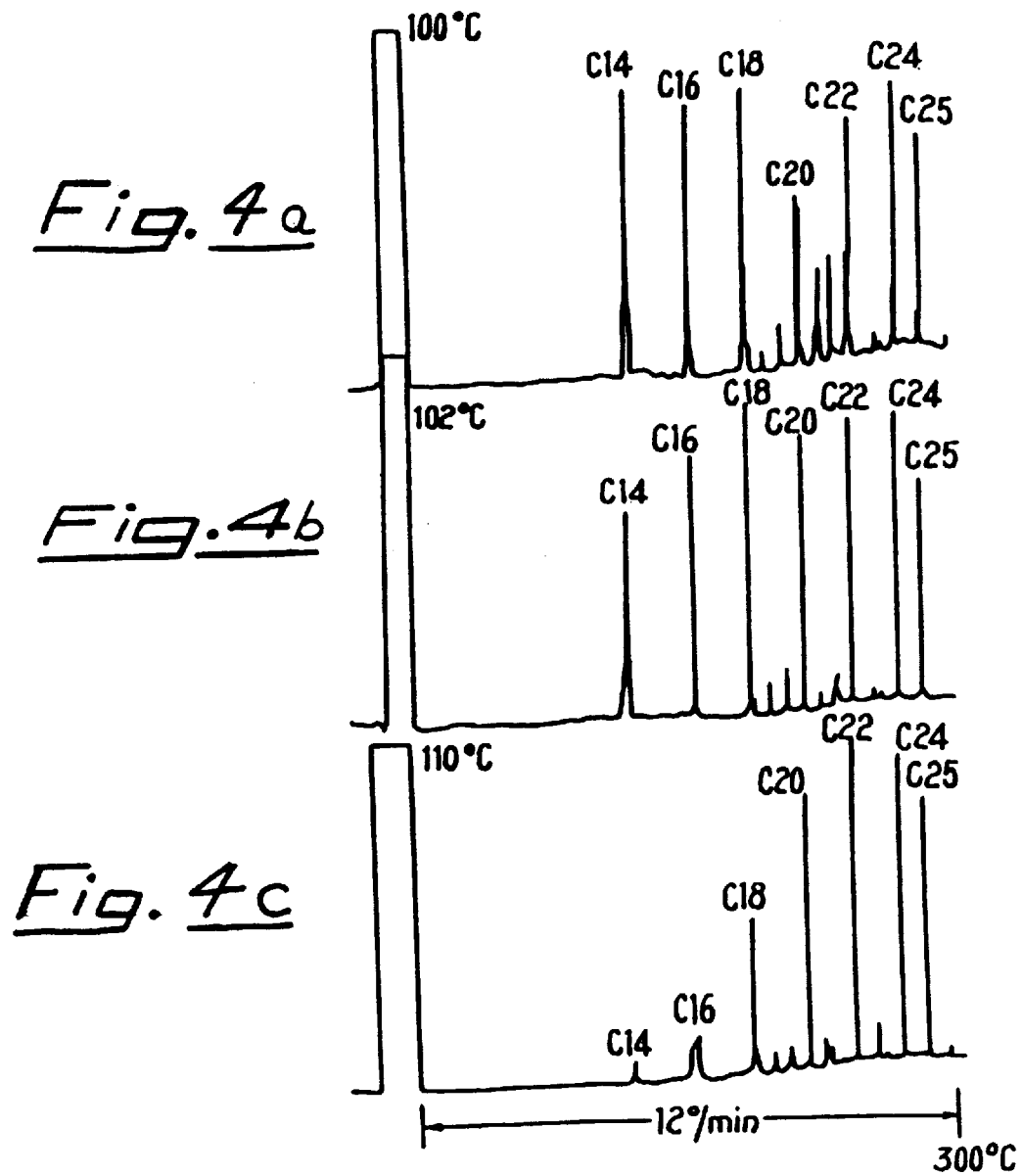

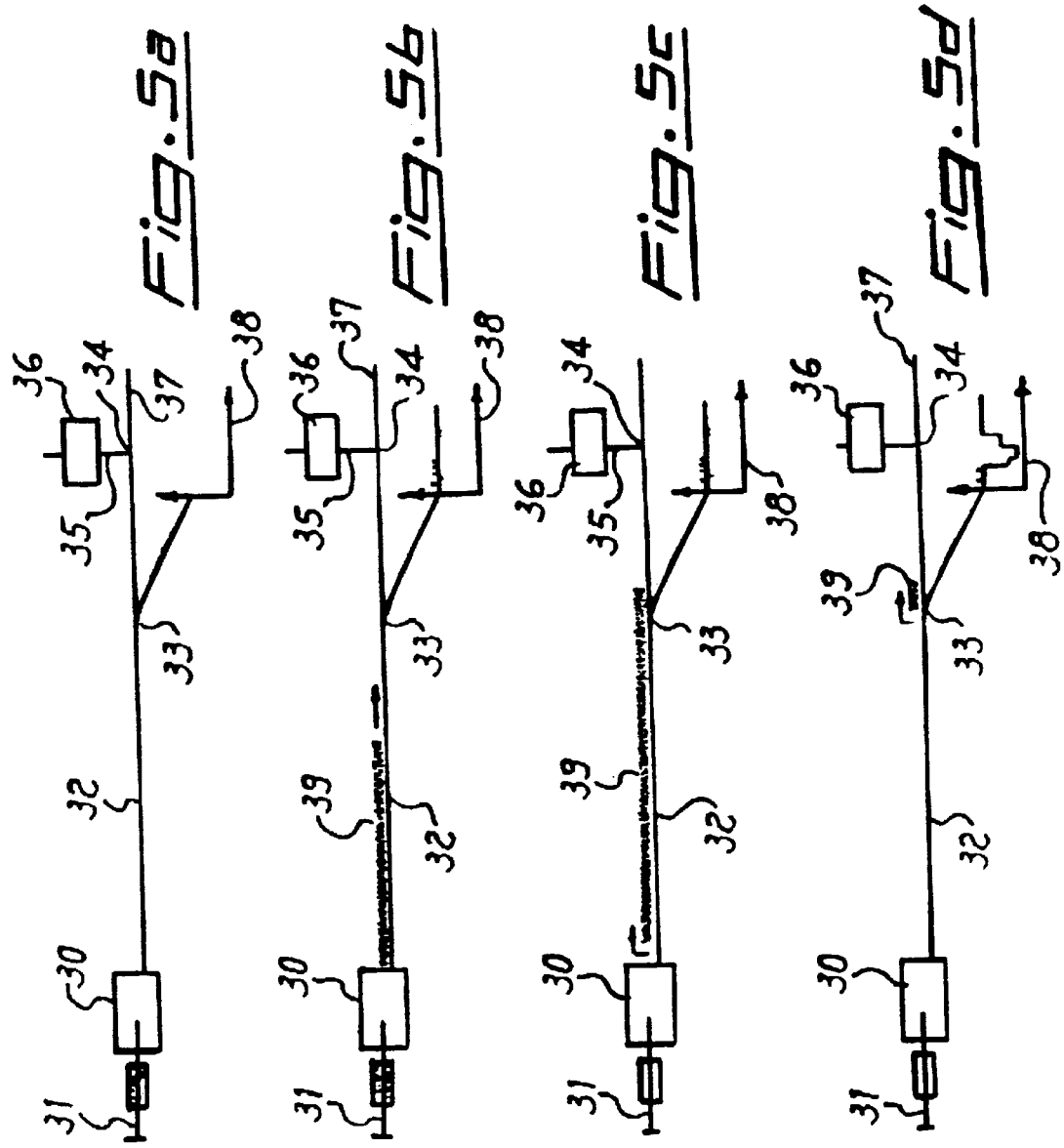

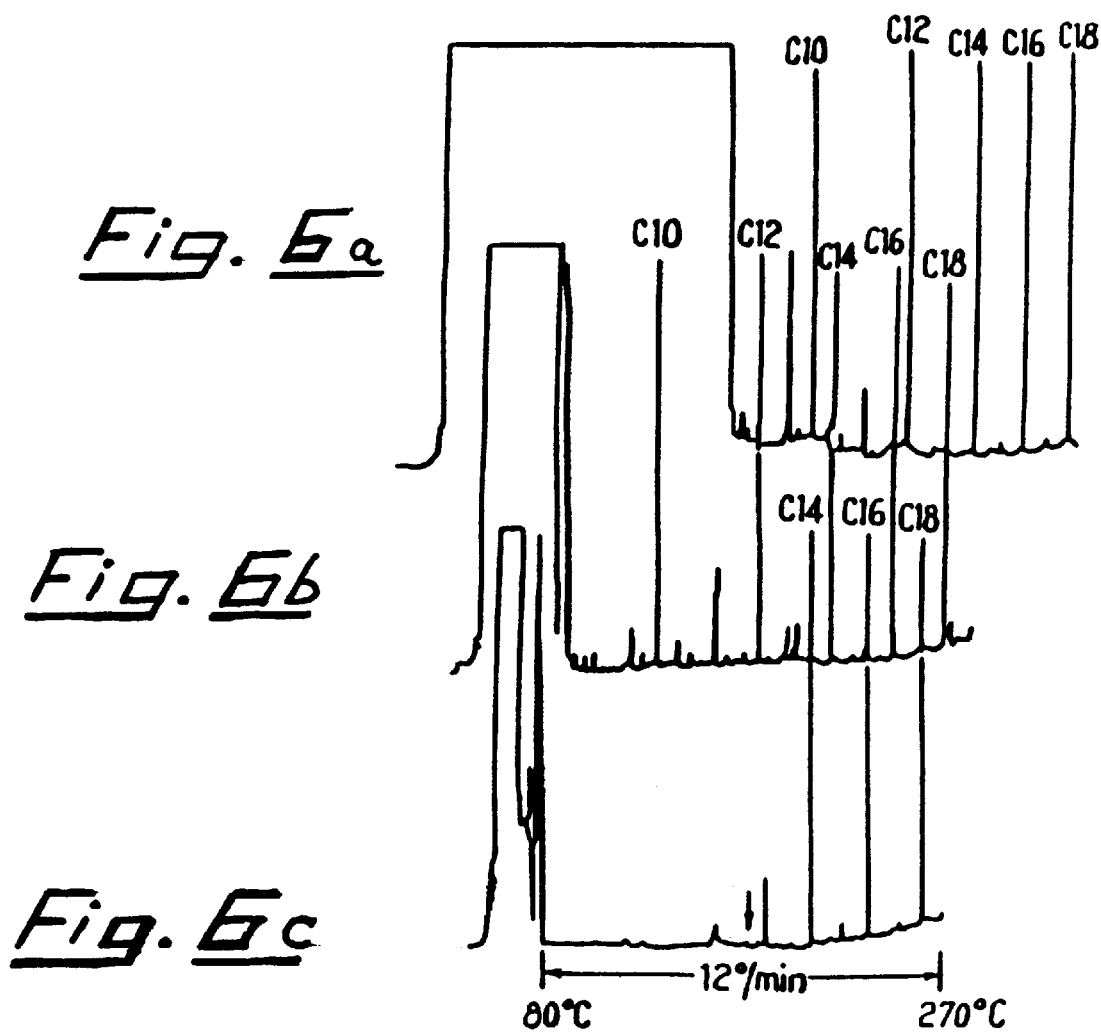

___ TEMPERATURE
___ PRESSURE

METHOD, DEVICE AND APPARATUS TO DETECT CHANGES OF STATE IN A CAPILLARY AND TO OPTIMIZE INJECTION CONDITIONS OF A SAMPLE INTO GAS-CHROMATOGRAPHY APPARATUSES

CROSS REFERENCE TO COPENDING PATENT APPLICATIONS

This is a continuation of PCT/EP98/03977 filed Jun. 30, 1998.

FIELD OF THE INVENTION

The present invention concerns a new method to determine if and when a solvent which, together with the substance being analyzed, constitutes the sample injected into a gas-chromatographic analysis apparatus, undergoes a change of state (evaporation or recondensation) inside a capillary tube and/or in correspondence to one or more pre-set points of the same. The invention also concerns methods to control and optimize the injection and introduction conditions of a sample into the analytical column of a gas-chromatographic apparatus, on the basis of information obtained by means of one or more detections indicating whether or not the above-mentioned change of state has occurred, as well also a device and an apparatus to obtain said detections and perform said control.

BACKGROUND OF THE INVENTION

As it is known, a gas-chromatographic analysis apparatus generally consists of an injector, an analysis column, an oven or chamber housing the column, and a detector. The most recent technical advances in this field have focused mainly on the phase preceding the true analysis, that is on the phase of injection of the sample (defined as the substance to be analyzed, diluted in a suitable solvent) which, pushed by a carrier gas, must be transferred to the analysis column under optimal conditions.

To this end, a variety of techniques have been developed, mainly and more generally including vaporization injection techniques and so-called direct on-column injection techniques.

According to the former techniques, the sample, introduced in a liquid state, vaporizes in a special, independently-heated chamber, and is then fed, in whole or in part, to the column or better to a so-called pre-column (with or without a stationary phase), inside of which pre-determined conditions are created—in particular in order to obtain that the sample undergoes or not (depending on the chosen operational methods) to a recondensation. The pre-column is usually housed in the same gas-chromatographic oven which houses the column, but a pre-column dedicated oven could be foreseen. Furthermore, when the sample undergoes recondensation, it is suitable to eliminate most of the vaporized solvent before the sample enters the analysis column, which can be performed by means of a discharge duct controlled by a valve and positioned downstream the pre-column and upstream the introduction point in the analysis column. This is especially important when, according to the most recent techniques, injections are performed with large volume samples.

In any case, these techniques require a detection that sample recondensation be effectively carried out, or not, in the column or pre-column, by determining in all cases the sample conditions, specially sample temperature conditions inside the column or pre-column, in order to obtain or not said sample recondensation.

Furthermore, it is often necessary to ensure that the pre-column temperature is very close to that causing the recondensation, i.e. slightly above or slightly below said temperature, in order to ensure the best analytical results.

When most of the solvent vapors are discharged downstream the pre-column, it is crucial that the closing time of the discharge valve is precisely choosen in order to avoid, on one hand, excess solvent in the column, resulting in longer and unuseful analysis times and, on the other hand, losing the most volatile compounds.

Finally, with some injection techniques, it is important to ensure that the length of column or pre-column which is wetted by the sample in its liquid state has a pre-determined size: in other words, it is important to know the quantity of liquid present in the column or pre-column, which obviously depends from the length of wetted capillary tube.

In order to obtain the best conditions for injecting and/or introducing the sample, it is of the utmost importance to be able to establish if and under what conditions the change of state (i.e. liquid-to-vapor or vapor-to-liquid) of the solvent or sample effectively takes place, either in the column or pre-column, or even in correspondence to one or more points along same, so as to use the information thereby obtained to optimize the control conditions of injection and/or introduction of the sample into the column.

DISCLOSURE OF THE INVENTION

Therefore, a main object of the invention is to provide a method for detecting the change of state of a solvent or sample (substance to be analyzed+solvent) inside a capillary tube or in one or more points along the same, said capillary tube being in particular a pre-column or a column belonging to a gas-chromatographic apparatus.

Another object of the invention is to provide a method for controlling the injection conditions of a sample in a gas-chromatography, so to optimize these conditions on the basis of information obtained by the afore-mentioned change of state detection.

Yet another object of the invention is to provide a device to detect said change of state inside a capillary tube or in one or more points along same, as well as a gas-chromatographic analysis apparatus, including at least one of the afore-mentioned detection devices and means to utilize the related information in order to optimize sample injection and/or introduction conditions in the same apparatus or in similar ones.

Finally, another main object of the invention is to provide, by means of the above-cited method and device, a behaviour model for the sample in a gas-chromatographic pre-column or column, according to the solvent used. This model can be expressed in the form of equations whose constants and/or parameters are experimentally determined and can be put into a software form, so that it may be used for analysis conducted on apparatuses without said means to detect the above-mentioned change of state.

According to the invention, a method is provided to detect any change of state (recondensation or evaporation) that occurs in an injected solvent—in case together with a substance to be analyzed—within a capillary tube of a gas-chromatographic apparatus, said method being characterized by the steps of measuring the temperature in correspondence of at least one point of said capillary tube, and/or the pressure, or flowrate of the carrier gas fed to said capillary tube, and of registering changes in said temperature, and/or in the gas pressure, or flowrate, which are detected when a solvent change of state at every temperature change detecting point and/or within the capillary tube occurs.

In particular, measurement of changes in pressure or flowrate of the carrier gas is carried out upstream of the capillary tube and indicates a total evaporation of the liquid in the capillary tube. A measure of temperature changes, on the other hand, is carried out by means of a thermal probe applied to the outside of the capillary tube, in correspondence to every point to be detected.

Furthermore, always according to the invention, in order to control and optimize the injection and/or introduction conditions of a sample, as formed by a substance to be analyzed dissolved in a solvent—in a gas-chromatographic analysis apparatus comprising an injector, an eventual pre-column, a separation column, a detector, an oven or chamber for the separation column, and an oven or chamber for the pre-column, coincident with or separate from the analysis column oven—at one or more pre-fixed points on the column or pre-column or respectively upstream of the same the external temperature of the column or pre-column, and/or the pressure, or flowrate of the carrier gas is measured and at least one of the parameters controlling the injection and/or introduction into the separation column is modified following the detection of changes in temperature, and/or pressure, or flowrate and consequently a change of state of the solvent or sample at said point or points of the column or pre-column, and/or in the column or pre-column itself, according to the above described method.

Always according to the invention and in order to control the sample introduction conditions in a gas-chromatographic analysis apparatus, as above defined, it is possible to measure, at one or more pre-fixed points on the column or pre-column, the external temperature of same, to vary at least one of the injection parameters until a change in temperature and then a change of state of the solvent or sample is detected at said point, according to the method described above, and modify at least one of the apparatus functional parameters on the basis of the information obtained.

Furthermore, according to the invention a method is provided for controlling and optimizing injection and/or introduction conditions of samples into the analysis column of a gas-chromatographic analysis apparatus, characterized by the creation of a mathematical model of the solvent or sample behaviour in a similar apparatus, by means of experimental detection of temperature changes in one or more points on the column or pre-column, and/or of pressure, or flowrate changes within the same, according to the described method, for each solvent in a range of solvents; and by the transformation of said mathematical model in a software that can be applied to the original gas-chromatographic analysis apparatus, without further measure of temperature, and/or pressure, or flowrate changes.

BRIEF DESCRIPTION OF THE DRAWINGS

The invention will be now described in greater detail with reference to examples of applications and to the attached drawings, in which:

FIGS. 4a–4c are a series of chromatograms as obtained under different temperature conditions inside the oven and showing the optimization possibilities according to the invention.

FIGS. 5a–5d diagrammatically show the operation of a solvent release valve under the control of a thermocouple.

FIGS. 6a–6c show a series of chromatograms obtained by varying the closure times of the solvent release control valve to demonstrate the optimization possibilities of said operation.

MODES OF CARRYING OUT THE INVENTION

As it is known, a change of state from liquid to vapor, or from vapor to liquid, always involves the absorption or the emission of a given heat quantity which obviously depends from the substance undergoing the change of state and the quantity of said substance. In particular, it has been ascertained that the evaporation of one microlitre of solvent requires a heat amount ranging from about 50 to 539 mcal; for solvents more commonly used in gas-chromatography, the heat amount is around 100 mcal/microlitre and this, taking into the account the thermal capacity of the capillary tube fused silica, leads to a reduction in temperature of about 1° C. per twenty mg of capillary tube. Of course, the opposite change of state, from vapor to liquid (recondensation), frees an equal amount of energy and involves a corresponding rise in temperature.

Actually, the weight of fused silica affected by a change of state occurring on a length of one cm is between one and two mg and then the temperature change would be greater. There are, however, various factors—such as the removal of heat by the carrier gas and the filtering effect due to the heat mass of the temperature measuring thermocouple—which reduce the size of the thermal signal due to the change of state. In any case, however, it has been ascertained that the temperature change due to said change of state is always discernible, even from outside the capillary tube.

Figure 1:
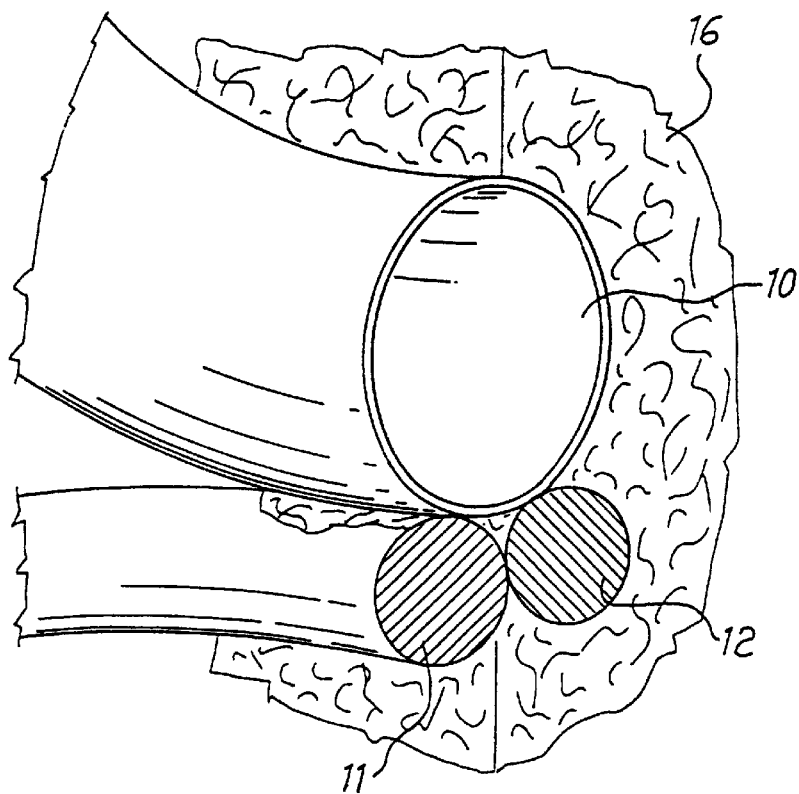
FIG. 1 shows, in an enlarged scale, methods for applying a thermocouple to the outside of a capillary tube, in order to measure the temperature of same.

In order to measure the temperature and then the changes thereof, it is suggested to use a thermocouple applied to the outside of the capillary tube, as shown in FIG. 1, wherein the thermocouple thermojunctions 11 and 12 are applied to the capillary tube 10 in any suitable way ensuring a good thermal contact with the capillary tube outer wall, while keeping at a minimum their thermal mass. The whole is then wrapped with heat-insulation insulating material 16 for protection against the outer temperature, i.e. the oven environment. The measure zone is about three cm long.

Figure 2:
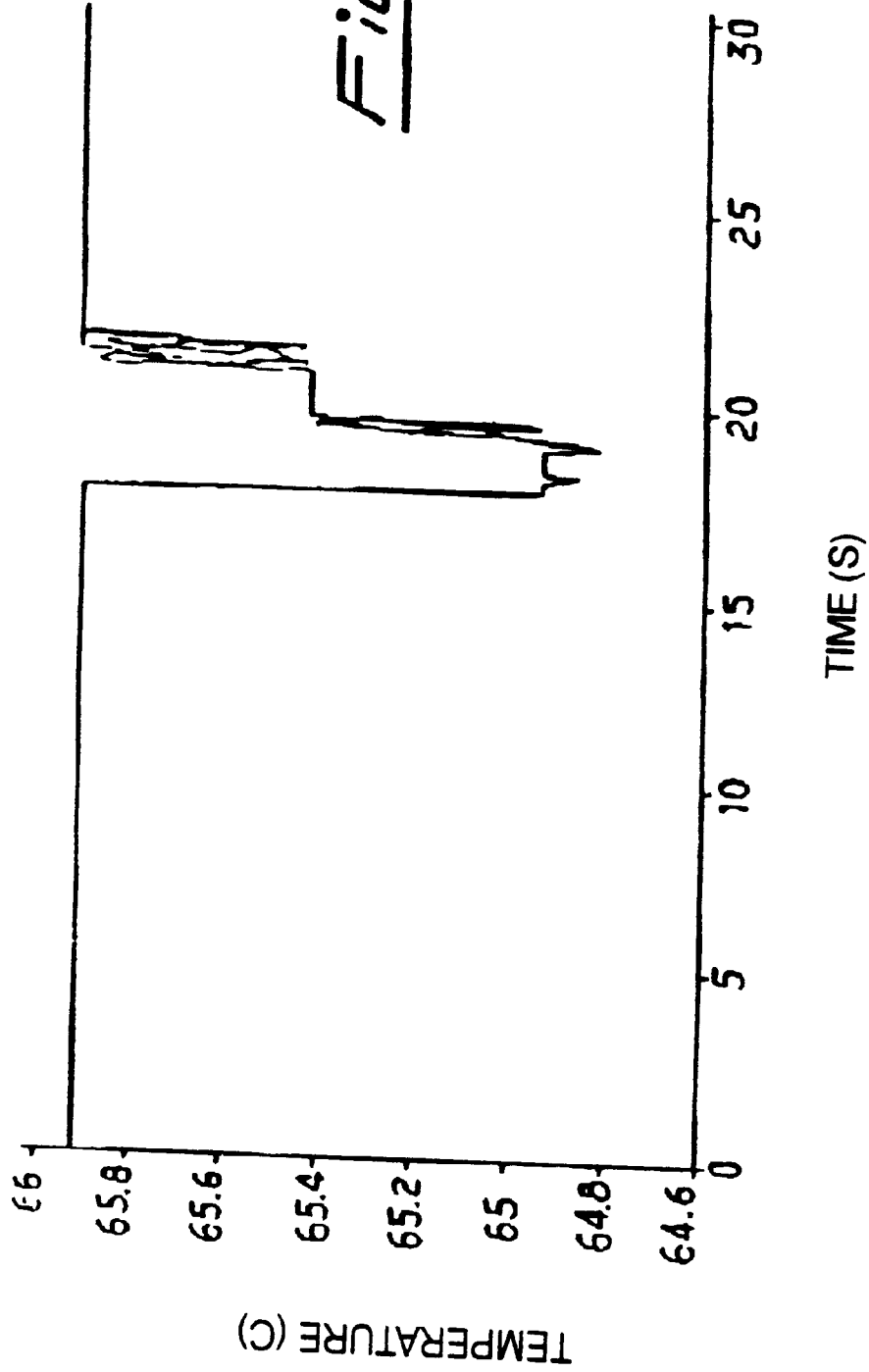
FIG. 2 shows the temperature changes as measured by an external thermocouple, when a change of state in the capillary tube occurs.

FIG. 2 shows a detection carried-out in case of a change of state (vaporization) of n-hexane, under the following conditions:

Pre-column length: 15.0 m

Carrier gas: hydrogen

Solvent: n-hexane

Vaporizing injector: 250° C.

Pre-column inner diameter: 0.53 mm

Carrier gas flowrate: 21 sccm

Injector-thermocouple distance: 5.0 m

Injected volume: 200 µl
Oven temperature: 60° C.
Injection speed: 20 µl/s

Figure 3:
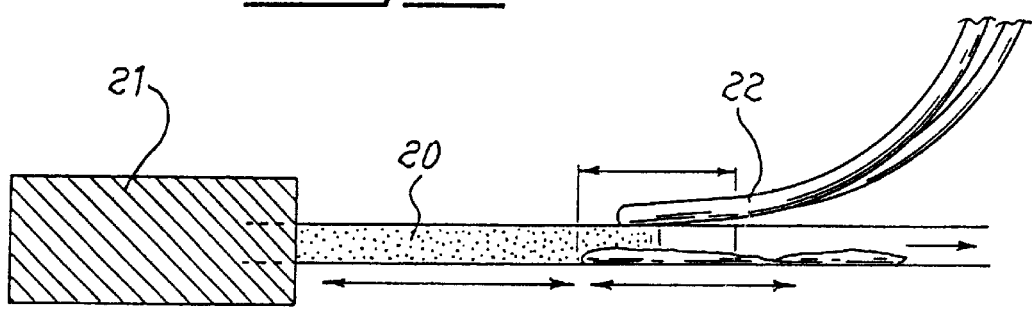
FIG. 3 diagrammatically shows an example of use of a thermocouple in measuring temperatures in a vaporization injection system.

In FIG. 2, the vertical axis shows temperatures in ° C. of the pre-column as measured at five meters from the injector and the horizontal axis times in seconds. In case of a sample introduction system of the vaporization type, as diagrammatically shown in FIG. 3, a pre-column 20 from a vaporization chamber 21 carries a thermocouple 22 of the above described type, applied to the pre-column at a given distance (from five to seven cm for example) from the vaporization chamber to avoid any influence by the carrier gas and hot vapors that leave the vaporization chamber.

In practising the invention, for example, the temperature of the oven housing the pre-column is changed until verifying that, in correspondence with the thermocouple, a temperature raise is detected, indicating that, at that particular point and under the pre-established operating conditions (type of solvent, pressure, and flow of carrier gas, etc.), a recondensation of the solvent vapors took place. On the basis of this information, it is then possible, depending on the foreseen modes of injecting the solvent or sample, to vary the temperature of the oven housing the pre-column either up or down and for preset values. For instance, in case a solvent recondensation is required, the indicated temperature level of the oven will be maintained or slightly lowered, while in case a recondensation is not wanted, the oven temperature will be raised—in some cases only a few degrees above the temperature at which recondensation occurred. Obviously, instead of changing the oven temperature, the same result can be obtained by varying at least one of the other parameters responsible for the sample injection conditions.

In other situations, such as so-called on-column type injections it is on the contrary important to control the length of the column or pre-column wetted zone, starting from the injector. In this case, the thermocouple is placed at the end of the column or pre-column length that is to be wetted and the oven temperature (or another parameter) is changed for instance until detection that a change of state with solvent vaporization occurred at the thermocouple application point, as indicated by a drop in the temperature detected by the thermocouple. In this case, the set oven temperature (or other parameter to be varied) will be at the desired value.

A carrier gas pressure or flow rate injector may be placed upstream of the sample injection device when the thermocouple is used in thermal contact with an outer surface of the column or pre-column.

FIGS. 4a-4c shows three chromatograms showing the importance of accurately determining the dew point when transferring the sample in an apparatus with vaporization chamber (according to FIG. 3) and without solvent recondensation. Two hundred microliter of n-alkanes in heptane were introduced in a three-meter long pre-column with a 0.32 mm inner diameter. The pre-column was connected to a twenty-meter separation column with a 0.25 mm inner diameter and to a solvent vapor outlet fitting having an inner diameter of 0.53 mm. With a hydrogen input pressure of forty kPa and flowrate of twenty ml/min through the vapor outlet before transfer, it has been established, using the invention method, a heptane dew point at 102° C. and three analyses were made, respectively: at 100° C. (upper chromatogram), at 102° C. (middle chromatogram), and at 110° C. (lower chromatogram).

Examining the chromatograms, it can be immediately ascertained that, when the oven temperature was lowered just 2° C. below the dew point, the rencondensated solvent passage through the pre-column generated a peak distortion, while increasing temperature 8° C. above the dew point caused a considerable increase in the loss of the most volatile compounds ($C_{14}$, $C_{16}$, and $C_{18}$).

It should be made clear that, even if the above described examples used changes in oven temperature, it is possible to vary parameters different than temperature, as the factors determining the solvent dew point are different.

Another important application of the method for determining whether a change of state has occurred concerns controlling the solvent vapor release valve, which is situated on an outlet branch between the gas-chromatographic pre-column and column. According to the current operating mode, the solvent vapors initially leaving the pre-column are released externally and it is extremely important to close the release valve at the right moment, in order to avoid excess solvent vapors from entering the column—which would unduly prolong the analysis—and to avoid losing the most volatile compounds together with the last solvent vapors.

In order to optimize the valve closure time, the invention foresees to position a thermocouple at a pre-determined point along the pre-column, for example at a distance equal to seventy percent of its length, starting from the injector side. The passage of the end of the liquid solvent or sample layer in correspondence of the thermocouple can be detected due to the cooling effect caused by the solvent evaporation. This information is then used to ensure that the solvent vapor release valve is closed precisely at the ideal moment.

The diagram is shown in FIGS. 5a–5d, wherein an injection chamber 30 of either the vaporization or on-column type is shown, in which the solvent or sample is introduced by the device 31 before entering into the pre-column 32. The thermocouple is positioned at a pre-fixed point 33 of the pre-column and downstream that point 33 a T-piece 34 deviates the solvent to a discharge duct 35 controlled by a valve 36, or the sample to the analysis column 37. The valve 36 is initially open and it is important, as before said, to close the same at the ideal moment. Before injection, when the pre-column is empty (FIG. 5a) and the valve 36 is open, the thermocouple does not provide any signal (in 38). During injection (FIG. 5b), the liquid zone 39 spreads into the pre-column and reaches the point 33 where the thermocouple has been applied (FIG. 5c), without any signal from the same. At the end of the injection, the liquid in the pre-column begins to evaporate from the back (FIG. 5c), following the carrier gas flow and when the rear end of the band of liquid reaches the thermocouple 33 (FIG. 5d), the latter registers a decrease in temperature following the evaporation of the solvent. This signal is used to control the closure of valve 36.

FIGS. 6a–6c shows three chromatograms obtained, starting from above, using staggered closure times of the vapor release valve—specifically, the first was six seconds in advance of the optimum time, the second was at the optimum time, and the third was delayed three seconds. In the first chromatogram, it can be immediately seen a large solvent peak (for example twelve minutes), which delays the completion of the analysis, while in the last chromatogram a considerable loss of volatile compounds ($C_{10}$, $C_{12}$) is detectable.

Another possible application of the principles of this invention is to use a single thermocouple at a point on the column or pre-column that will be wetted by the solvent or liquid sample, and which is at a known distance d from the injector. Using the invention to register the instant in which a change of state occurs at that point, and knowing the injected volume and the injection speed, it is possible to know the pre-column capacity and vaporization speed, then calculate and set the optimum parameters for the injection and/or transfer to the analysis column: in particular, the injection speed, the oven temperature, and the solvent vapor release valve closure time.

This technique may be used to study the behaviour of the liquid in the column or pre-column, by varying for instance the injection speed of the sample or solvent until obtaining a signal from a thermocouple positioned at a pre-fixed point on the column or pre-column—at a distance (L) from the injector. This means that the liquid will wet the point where the thermocouple has been positioned, and perhaps extends slightly beyond. By registering said speed (uj) and the time elapsed from the end of the injection to the thermocouple signal appearance (tvap)—i.e. the time needed for a complete vaporisation of the liquid in the column or pre-column—and knowing the injected volume (Vj) and the distance (L) of the thermocouple from the start of the column or pre-column, it is possible to calculate the parameters that regulate the behaviour of the fluid in the column or pre-column (∅) and, in particular, the capacity of the column or pre-column, as measured in L/m, and the vaporization rate (Rvap).

Indeed, the volume of liquid (Vliq) remaining in the column or pre-column at the end of injection is:

$$Vliq = (uj - Rvap) * tj \tag{1}$$

where tj is the injection time.

From (1)

$$L * \phi = \left(uj - \frac{L * \phi}{tvap}\right) * \frac{Vj}{uj} \tag{2}$$

From (2), it is possible to obtain ∅

$$\phi = \frac{uj * Vj * tvap}{L * (uj * tvap * Vj)} \tag{3}$$

and therefore Rvap $$Rvap = \frac{L * \phi}{tvap} \tag{4}$$

The experiments described above were repeated by the Applicant, by monitoring not only the temperature but also the pressure at the start of the column or pre-column, operating in a constant carrier gas flow mode. The experiments were conducted under the following conditions:

pre-column length: 15 m
pre-column inner diameter: 0.53 mm
solvent: n-hexane
carrier gas: hydrogen
on-column injector
valve SVE (solvent vapor exit) open
carrier gas florate constant: 21 sccm
distance injector-thermocouple: 5 m
volume of sample injected: 200 µl
oven temperature: 47° C.

Figure 7:
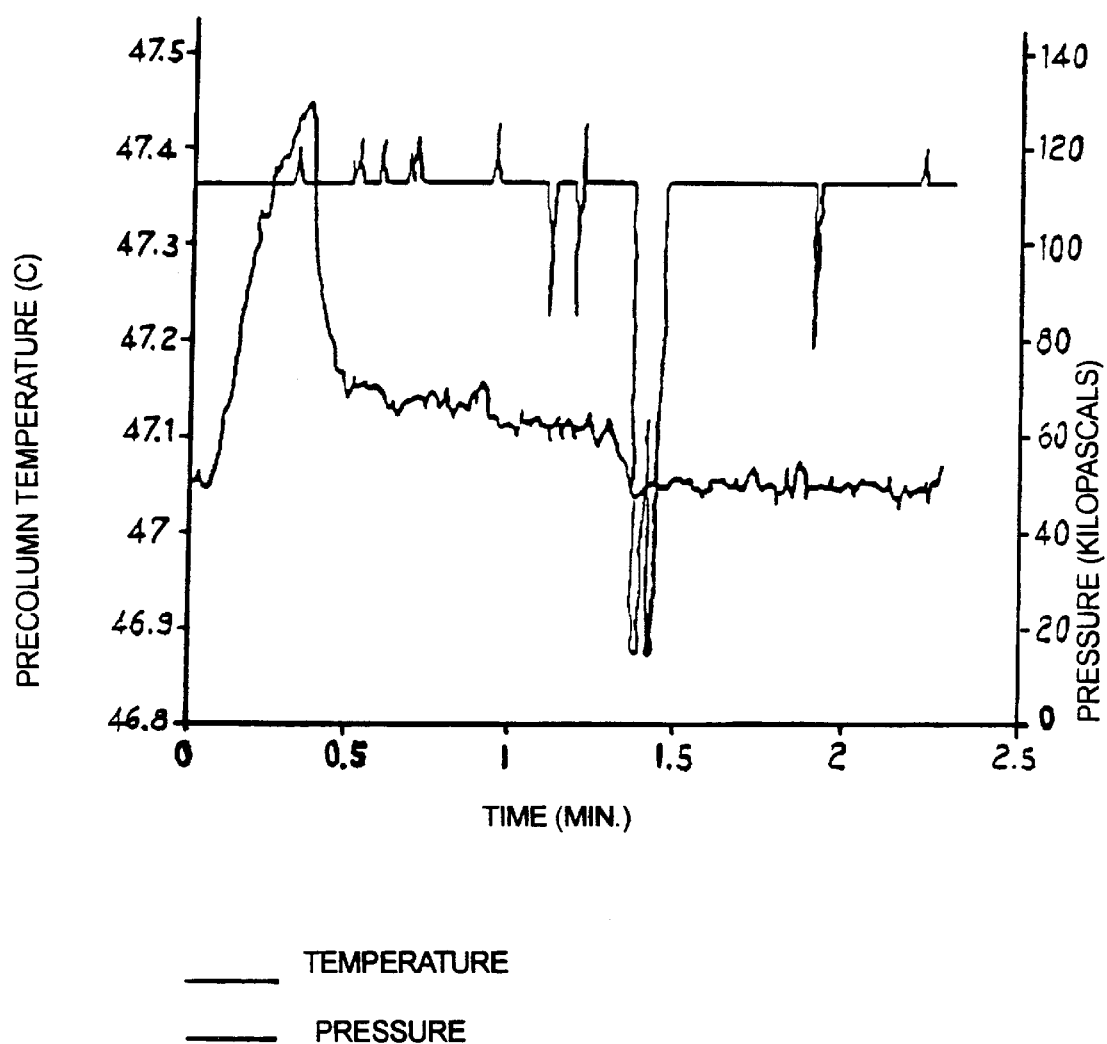
FIG. 7 is a diagram showing the carrier gas pressure changes occurring when a completion of the vaporization of a liquid in a pre-column is detected by means of a temperature measure.

A result of said monitoring is the graph shown in FIG. 7, executed with oven temperature at 40° C., which shows how the pressure, after an initial peak due to the movement of the injection needle entering into and leaving the column or pre-column, reaches a higher value than the initial one due to the different viscosity of the mixture carrier gas/solvent vapors, as compared to that of the carrier gas alone. Subsequently, a decrease in pressure from the initial level is observed, precisely in correspondence to the change in temperature detected by the thermocouple, i.e. in correspondence to the depletion of the liquid inside the column or pre-column.

Using the invention, it is possible therefore to establish behavioural parameters for the fluid in the column or pre-column, not only by detecting changes in temperature along the same, but also, together with or as an alternative to, by detecting changes in the carrier gas pressure upstream the column or pre-column. The only difference in information is the fact that when detecting pressure changes it is not possible to establish what point the liquid will arrive at in the column or pre-column but only the time elapsed until it is eliminated.

In case where the pressure is measured, equation (2) becomes $$Vliq = \left(uj - \frac{Vliq}{tvap}\right) * \frac{Vj}{uj} \tag{2'}$$

from which $$Vliq = \frac{uj * Vj * tvap}{uj * tvap + Vj} \tag{5}$$

$$Rvap = \frac{Vliq}{tvap} \tag{6}$$

In operation with carrier gas at a constant pressure, the depletion of the liquid in the column or pre-column can be measured also by means of (positive) changes in the flowrate at the column or pre-column head; in this case equations (2'), (5) and (6) are still valid.

In light of the above, it appears that the described technique for detecting changes of state in samples by measuring changes in temperature, and/or pressure, and/or flow, enables one to build up a mathematical model of the behaviour of a sample in a given gas-chromatographic apparatus, as a function, of course, of the solvent used. Indeed, experimental data obtained from temperature changes in one or more points of the column or pre-column, and/or from changes in pressure or flow due to the depletion of the liquid within the same, can be used to calculate the constants and the parameters of the model equations. This mathematical model could subsequently be expressed in the form of a software, which is able to run gas-chromatography apparatuses similar to the one from which the model itself was obtained, by choosing the optimum conditions of sample injection and transfer for each solvent used, no longer having to register changes in temperature and/or pressure or flow.

What is claimed is:

1. A method for detecting a change of state (recondensation or evaporation) of an injected solvent—in case together with a substance to be analyzed—within a capillary tube of a gas-chromatographic apparatus, characterized by the steps of measuring the temperature in correspondence with at least one point of said capillary tube, and/or the pressure, or flowrate of the carrier gas fed into the capillary tube, and of registering changes in said temperature, and/or said gas pressure or flowrate, which are detected when a solvent change of state occurs at every temperature change detecting point and/or within the capillary tube, said temperature change being detected by means of a thermal probe applied to an outside of said capillary tube, at each point to be checked.

2. A method according to claim 1, characterized in that said change in the carrier gas pressure or flowrate is detected upstream of said capillary tube and indicates a complete evaporation of the solvent present in said capillary tube.

3. A method for controlling and optimizing the injection and/or introduction conditions of a sample, as formed by a substance to be analyzed dissolved in a solvent, in a gas-chromatographic analysis apparatus consisting of an injector, an eventual pre-column, a separation column, a detector, an oven or chamber for the separation column, and a oven or chamber for the pre-column, coincident with or separate from an analysis column oven, characterized in that at one or more pre-fixed points on the column or pre-column, or respectively upstream of the same, the external temperature, of the column or pre-column and/or pressure, or flowrate of the carrier gas is measured and at least one of the parameters controlling the injection and/or introduction into the separation column is modified following the detection of changes in temperature and/or pressure or flowrate and consequently following a change of state in the solvent or sample at said point or points of the column or pre-column, and/or in the column or pre-column itself, the control parameter being the closure command of a solvent vapor release valve upstream of said analysis column, characterized in that temperature changes at a detection point on the column or pre-column near the end of the same are detected, and in that said closure command is sent to said valve upon detection of a change of state from liquid to vapor at the detection point.

4. A method according to claim 3, characterized in that pressure or flowrate changes in the column or pre-column are detected; in that the instant in which said changes are detected, indicating a corresponding change of state when the liquid has been eliminated in the column or pre-column, is stored; and in that said closure command is sent to said valve according to times correlated to the detected instant.

5. A method according to claim 3, for which the sample is a liquid sample, characterized in that changes in temperature, and/or pressure, or flowrate are detected at a point on the column or pre-column having a pre-fixed distance from the injector, or respectively upstream of the column or pre-column; and in that parameters of injection and/or introduction of the liquid sample into the analytical column are calculated on the basis of solvent or liquid sample vaporization rate, as obtained from times of said detection and from the knowledge of the volume of the solvent or liquid sample injected, and the injection speed.

6. A method according to claim 5, characterized in that the instant at which vaporization of the solvent in the column or pre-column terminates is detected by means of said detection of temperature, and/or pressure, or flowrate changes; and in that the capacity of the column or pre-column and/or the vaporization rate of the solvent are calculated on the basis of said detection, the injected volume, and the injection speed.

7. A method according to claim 6, characterized in that the detection of pressure changes is performed while operating at a constant carrier gas flowrate.

8. A method according to claim 6, characterized in that the detection of flowrate changes is performed while operating at a constant carrier gas pressure.

9. A method for controlling and optimizing the conditions under which a sample is injected and/or introduced into an analytical column of a gas-chromatographic analysis apparatus, characterized in that a mathematical model of the behavior of the solvent or sample in a similar apparatus is created by experimentally detecting changes in temperature, and/or pressure, or flowrate at one or more points on a column or pre-column, or respectively in the same; and in that said mathematical model is transformed in a software that is applied to the gas-chromatographic analysis apparatus, without further detection of temperature, and/or pressure, or flowrate changes.

10. A method according to claim 9, characterized in that changes in temperature and/or pressure or flowrate are detected, and in that the parameters of said mathematical model are calculated.

11. A method for controlling and optimizing the injection and/or introduction conditions of a sample, as formed by a substance to be analyzed dissolved in a solvent, in a gas-chromatographic analysis apparatus consisting of an injector, an eventual pre-column, a separation column, a detector, an oven or chamber for the separation column, and an oven or chamber for the pre-column, coincident with or separate from the analysis column oven, characterized in that, at one or more pre-fixed points on the column or pre-column, the external temperature of the column or pre-column is measured; in that at least one injection parameter is changed until detecting a temperature change and consequently a change of state in the solvent or sample at said point, and in that at least one of the apparatus functional parameters is modified on the basis of the information obtained.

12. A device for carrying out the method according to claim 2, characterized by a carrier gas pressure or flowrate detector placed upstream of a column or pre-column.

13. A device for carrying out the method according to claim 1, characterized by a thermocouple placed in thermal contact with an outer surface of a capillary tube at at least one pre-fixed point on said column or pre-column, means for thermally insulating the thermocouple from the outside environment, and means for detecting changes in temperature as registered by said thermocouple.

14. A gas-chromatographic analysis apparatus for carrying out the method according to claim 11, characterized by at least one of a thermocouple and a carrier gas pressure or flowrate detector as well as means for varying at least one control factor of the solvent or sample injection or introduction.

15. An apparatus according to claim 14, of the type comprising at least a discharge line for discharging solvent vapors, upstream of the separation column, as well as valve means for controlling said discharge line, characterized in that said means for varying at least one control factor of the solvent or sample injection or introduction act on said valve means.

16. An apparatus according to claim 14, characterized by a carrier gas pressure or flowrate detector, placed upstream of the sample injection device.

17. An apparatus according to claim 14, characterized by at least the thermocouple applied in a position near an initial portion of the column or pre-column, immediately downstream of a solvent or sample vaporization chamber.

18. An apparatus according to claim 14, characterized by at least the thermocouple applied at a point on the column or pre-column where a solvent or sample change of state should occur during the injection process.

19. An apparatus according to claim 14, characterized by at least the thermocouple applied at a point on the column or pre-column where the thermocouple to be checked when, during injection of the solvent or sample, a change of state occurs.

20. A gas-chromatographic analysis apparatus characterized in that the sample injection and/or introduction conditions are optimized on the basis of a software obtained and applied according to the method of claim 9.

21. An apparatus for detecting a change of state of an injected solvent within a capillary tube of a gas-chromatographic apparatus, comprising:

means for measuring a parameter selected from a group consisting of temperature in correspondence with at least one point of said capillary tube and pressure or flowrate of a carrier gas fed to the capillary tube; and means for registering changes in the parameter that are detected in response to a change of state of the injected solvent that occurs at either every temperature change detecting point or within the capillary tube.

* * * * *